(12) United States Patent
You (10) Patent No.: US 8,590,393 B2
(45) Date of Patent: Nov. 26, 2013

(54) MULTI FUNCTION TEST METHOD AND STATION FOR GOLF CLUB SHAFTS

(76) Inventor: Daniel You, Anaheim, CA (US)

(*) Notice: Subject to any disclaimer, the term of this patent is extended or adjusted under 35 U.S.C. 154(b) by 255 days.

(21) Appl. No.: 12/986,833

(22) Filed: Jan. 7, 2011

(65) Prior Publication Data
US 2012/0073383 A1  Mar. 29, 2012

Related U.S. Application Data

(60) Provisional application No. 61/387,787, filed on Sep. 29, 2010.

(51) Int. Cl.
*G01N 3/22* (2006.01)
(52) U.S. Cl.
USPC .......................................... 73/847; 73/65.03
(58) Field of Classification Search
USPC ................... 73/841, 847, 65.03, 947
See application file for complete search history.

(56) References Cited

U.S. PATENT DOCUMENTS

| | | | |
|---|---|---|---|
| 4,212,193 A | 7/1980 | Turley | |
| 4,682,504 A | 7/1987 | Kobayashi | |
| 4,848,769 A * | 7/1989 | Bell et al. | 473/140 |
| 5,379,641 A | 1/1995 | Paasivaara et al. | |
| 5,429,008 A | 7/1995 | Matsumoto et al. | |
| 5,435,187 A * | 7/1995 | Ewy et al. | 73/856 |
| 5,515,717 A | 5/1996 | White | |
| 5,739,411 A * | 4/1998 | Lee et al. | 73/12.13 |
| 6,405,595 B1 | 6/2002 | Harrison | |
| 6,532,818 B2 * | 3/2003 | Blankenship | 73/579 |
| 6,571,640 B2 | 6/2003 | Harrison | |
| 7,195,565 B2 * | 3/2007 | White et al. | 473/296 |
| 7,788,982 B2 * | 9/2010 | Dee et al. | 73/851 |
| 2002/0139195 A1 | 10/2002 | Harrison | |
| 2010/0313672 A1 | 12/2010 | Dee et al. | |

OTHER PUBLICATIONS

Prior Patent Application for Shaft Flexibiliity Measuring Device, First named inventor Daniel You. Filed Mar. 5, 1999. Assigned to Apache Golf, Inc.
Multi-Matching Shaft Analyzer, PM-1000 Professional Series, Apahce Golf, Inc. 1999, pp. 1-28.

* cited by examiner

*Primary Examiner* — Max Noori
(74) *Attorney, Agent, or Firm* — Stetina Brunda Garred & Brucker; Lowell Anderson

(57) ABSTRACT

A test station for testing golf clubs has a clamp on the lower portion holding a shaft extending along a first axis. Sensors along that axis detect shaft vibrations torsion vibrations. Four towers are movably connected to a rail extending along the top portion of the base. Two of the towers have a first vertically adjustable shaft positioner and a device to detect forces exerted on the first shaft positioners. The other two towers also have vertically adjustable shaft positioners. The towers are used to determine stiffness, center of gravity, swing point and other properties. A drawer in the base contains a scale to measure the club length, and a pivoted stop to measure head angle.

22 Claims, 9 Drawing Sheets

MULTI FUNCTION TEST METHOD AND STATION FOR GOLF CLUB SHAFTS

CROSS-REFERENCE TO RELATED APPLICATIONS

This application claims the benefit under 35 U.S.C. §119(e) of Provisional Patent Application No. 61/387,787 filed Sep. 29, 2010, the complete contents of which are incorporated herein by reference.

BACKGROUND

Golf club shafts made of tapered metal, graphite composite tubes or other materials should be inspected to ensure material properties and shaft performance are within specified requirements. Currently a number of tests performed on golf club shafts are performed at separated test stations, most of which requires transporting the shaft to the location of each test station, removing the shaft from the transport mechanism, testing the shaft and returning approved shafts to the same or another transport mechanism. The transportation, removal and placement steps are time consuming and inefficient and risk damaging the shafts during transportation, removal from the transport mechanism and replacement in the transport mechanism. Further, the equipment takes up a lot of room making it unsuitable for travel along a golf tour. Moreover, the time to perform each of the various tests is time consuming.

BRIEF SUMMARY

A test station is provided for testing golf clubs. The test station has an elongated base with a lower portion and a top portion. A clamp on the lower portion holds a shaft extending along a first axis. A vibration sensor on that axis detects shaft vibrations and a torsion sensor detects shaft torsion about that first axis. First, second, third and fourth towers sequentially located and movably connected to a rail extending along the top portion of the base. The first and third towers each have a first vertically adjustable shaft positioner and a device for detecting forces exerted on the first shaft positioners. The second and fourth towers each have a second vertically adjustable shaft positioners. The shaft positioneers and force detectors are used to determine stiffness, center of gravity, swing point and other properties. A drawer in the base contains a scale to measure the club length, and a pivoted stop to measure the lie angle of the head.

A multi-function test station for golf club shafts is provided. The test stations has a housing with a generally horizontal lower portion joined to an inclined wall joined to a generally horizontal upper portion. A rail extends along a length of the upper portion. Four towers are mounted to the rail and configured to cooperate with the shape of the rail to move along at least a portion of the length of the rail. Each tower has a shaft positioning device oriented to center a longitudinal axis of the shaft in a common, substantially vertical plane. Each shaft positioning device is vertically adjustable in position. The test station also includes a force detecting device in each of two of the towers, with the force detecting device detecting the force exerted on the shaft positioning device in the substantially vertical plane. A display device is provided that is in electronic communication with at least one of the force detecting devices to visually indicate the force detected by the at least one force detecting devices. A fastening mechanism on each tower releasably fastens one of the respective towers to the rail. An end stop is mounted to the rail or the upper housing portion and extends across a portion of the substantially vertical plane. This arrangement allows multiple tests of the shaft and club to be performed.

In further variations, the test station may also have two of the shaft positioning devices configured to support a golf club shaft only from below the shaft, and two of the shaft positioning devices configured to engage the golf club shaft from at least the upper side of the shaft and preferably also engage the shaft from a lower side of the shaft at the end of the shaft.

The shaft positioning device advantageously comprises a pair of rollers rotating on parallel but offset axes, with the rollers having cross sections that narrow to a reduced area at the outer periphery. The rollers are spaced apart enough so they do not abut each other but close enough so the shaft cannot pass between them and rolls freely as the rollers rotate about their axes. rollers preferably have cross sections that narrow to a reduced area at the outer periphery.

The multi-function test station may optionally also have a pair of spaced apart jaws, with each jaw having an upper and lower jaw and a notch aligned along a longitudinal axis and sized to clamp onto the shaft during use of the test station. An actuating mechanism is provided to actuate the jaws to open to receive a golf club shaft in the notches and to close on the golf club shaft to hold the shaft along the longitudinal axis during use. The test station may further have a pair of posts on opposing sides of the longitudinal axis with at a vibration sensor located on at least one of the posts to determine the vibration frequency of a shaft extending along the longitudinal axis during use of the test station.

Moreover, a sensor track can be connected to the lower portion and located to extend along a generally vertical plane through the longitudinal axis. A support stand has a first end movably connected to that sensor track to move along that sensor track. The stand has an opposing end to which is fastened a shaft positioning device advantageously comprising the paired rollers described above and in more detail below, with the rollers being vertically positionable relative to the support stand to support the bottom of a shaft during use of the multi-function test station. Further, the stand may have a drawer containing a weight configured to be releasably fastened to the end of a golf club shaft to help determine vibration and/or bending and stiffness characteristics of the shaft during use of the test station.

The test station also may have a torsional frequency sensor on the housing or one of the towers. The drawer may also hold a torsional weight configured to be releasably fastened to the end of a golf club shaft during use of the test station. The torsional weight has a surface that interacts with the torsional frequency sensor to detect torsional frequency of a shaft to which the torsional weight is fastened during use of the test station.

The drawer is preferably a pull-out drawer located below the lower portion of the housing and extendable laterally away from the rail. The drawer may have a linear scale extending along a length of the drawer with a rotating stop at one end of the scale to align with an inclined portion of a club head mounted to the shaft. The linear scale advantageously has an alignment mechanism to align the shaft along the scale when an inclined head is aligned with the rotating stop. The rotating stop may include two stops at 90° to each other rotating about a pivot point at the end of the linear scale, and further comprising an angular scale centered on the pivot point with visible indicia reflecting the angle of each stop relative to a line perpendicular to the linear scale.

In a further embodiment, the test station for testing golf clubs has an elongated base with a first lower portion and a top portion vertically and horizontally offset from the first portion. A clamp on the lower portion is configured to releasably hold an end of a golf club shaft so the shaft extends along a first axis. A vibration sensor is located along the first axis to detect vibration of a shaft positioned along that first axis. The vibration sensor is in communication with a vibration display on the base to display vibration information during use. A torsion sensor is located on the base to detect torsion of a shaft positioned along that first axis. The torsion sensor is in communication with a torsion display on the base to display torsion information during use. The test station also has first, second, third and fourth towers sequentially located and movably connected to a rail extending along the top portion of the base. The first and third towers each have a first vertically adjustable shaft positioner and also has a device to detect forces exerted on the first shaft positioner along a vertical axis. The second and fourth towers each have a second vertically adjustable shaft positioned. The devices that detect forces are each in communication with a display to display the forces detected during use.

This further embodiment of the test station may have at least some of the shaft positioners comprising the paired of rollers on parallel axes spaced apart a distance sufficient to allow a shaft to rest on the rollers between the axes and freely rotate with the rollers. Further, the towers may each have a quick release connection to releasably fasten the tower to the rail. An elongated drawer may be provided in the base, below the lower section. The drawer may have a linear scale extending along a length of the drawer with an angular measurement device at one end of the scale to measure the length of the club shaft and the angle of a golf club head on that shaft. The angular measurement may have a rotating flange rotating about a point on an axis extending along the scale and has the flange located to abut the golf club head during use, with angular inclinations located below the rotating flange to allow determining the head angle. The drawer may further contain an oscillating weight configured to attach to an end of a golf club shaft during use to impart torsional rotation to the shaft. The test station may also have an end stop connected to the rail with a quick connect mechanism. The end stop may have a releasable connection allowing the stop to rotate its position to avoid interference with a shaft extending along a length of the top.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Referring to FIGS. 1-4, a testing station 10 for golf club shafts 12 is shown. The shaft 12 is typically a tapered, hollow shaft having a larger diameter grip end 14 and a smaller diameter head end 16 and extends along an axis 18. Depending on the state of assembly there may or may not be a head 17 (FIG. 11) on the end of shaft 12. The shafts 12 are currently made of metal or composite materials such as graphite epoxy composites, but other materials can be used.

Figure 1:
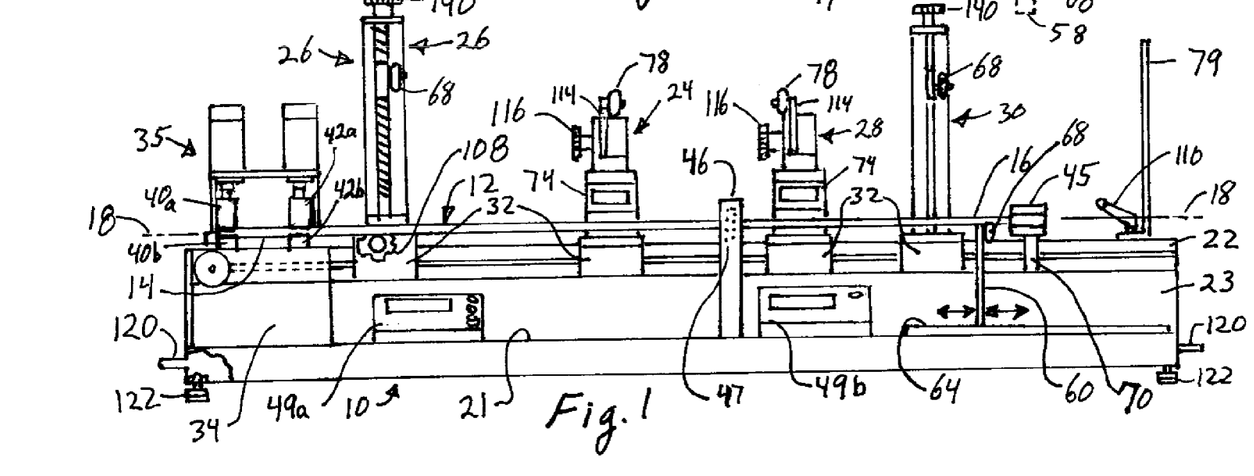
FIG. 1 shows a front plan view of a multi-function testing station for golf club shafts.
Figure 2:
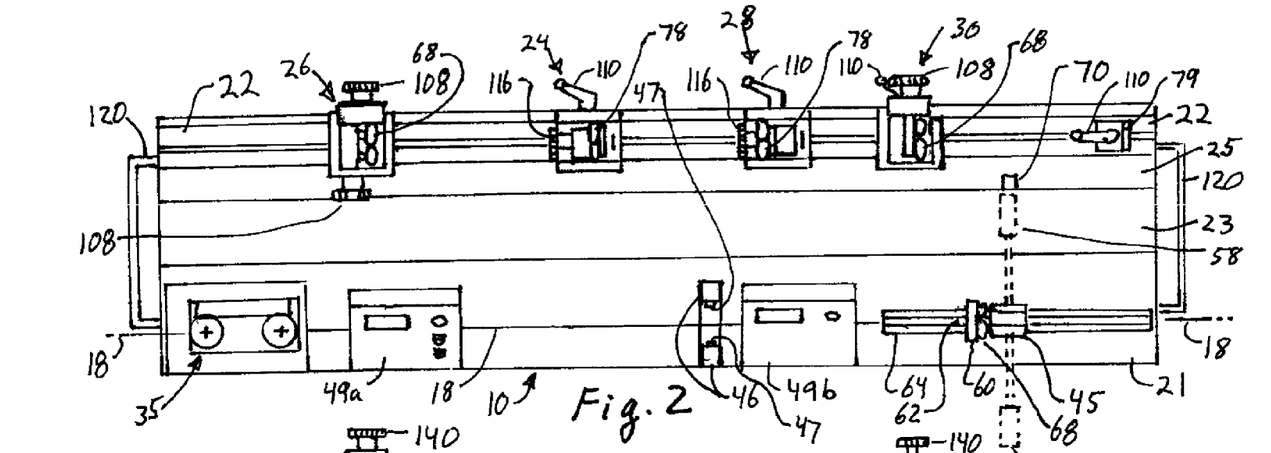
FIG. 2 shows a top plan view of FIG. 1, but without a shaft in position and with a torsion device in broken lines.
Figure 3:
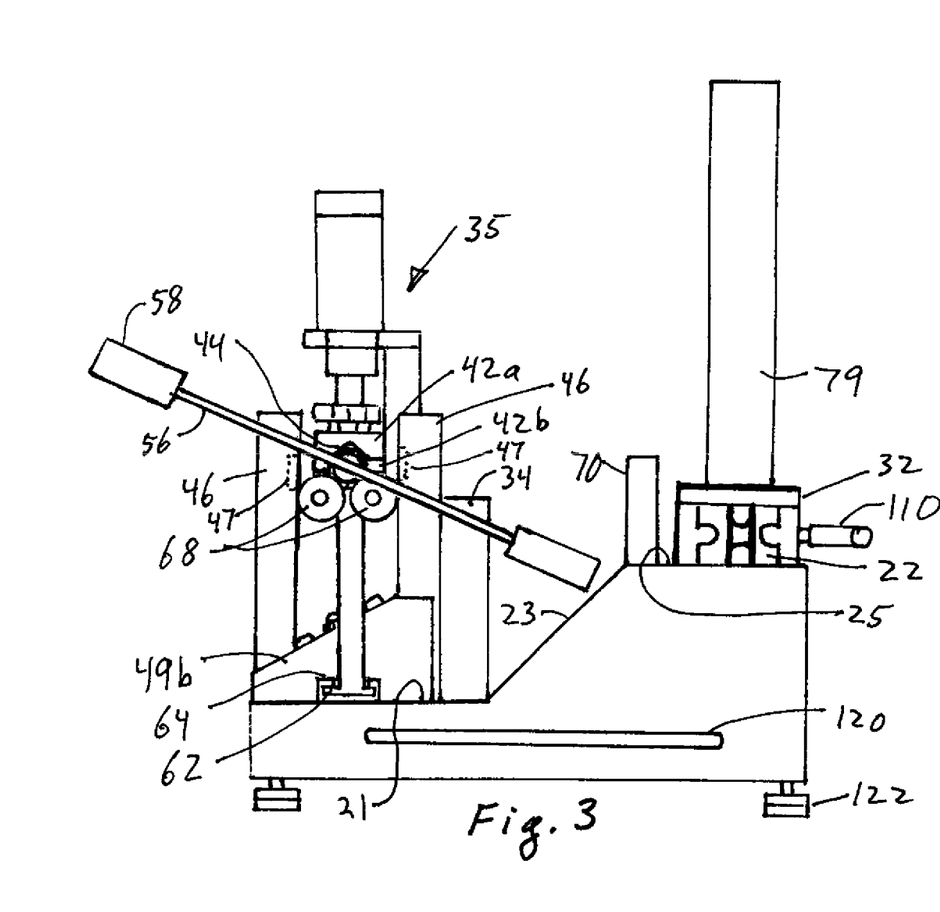
FIG. 3 shows an end plan view of the testing station of FIG. 2 with a shaft and torsion device, and no towers.
Figure 4:
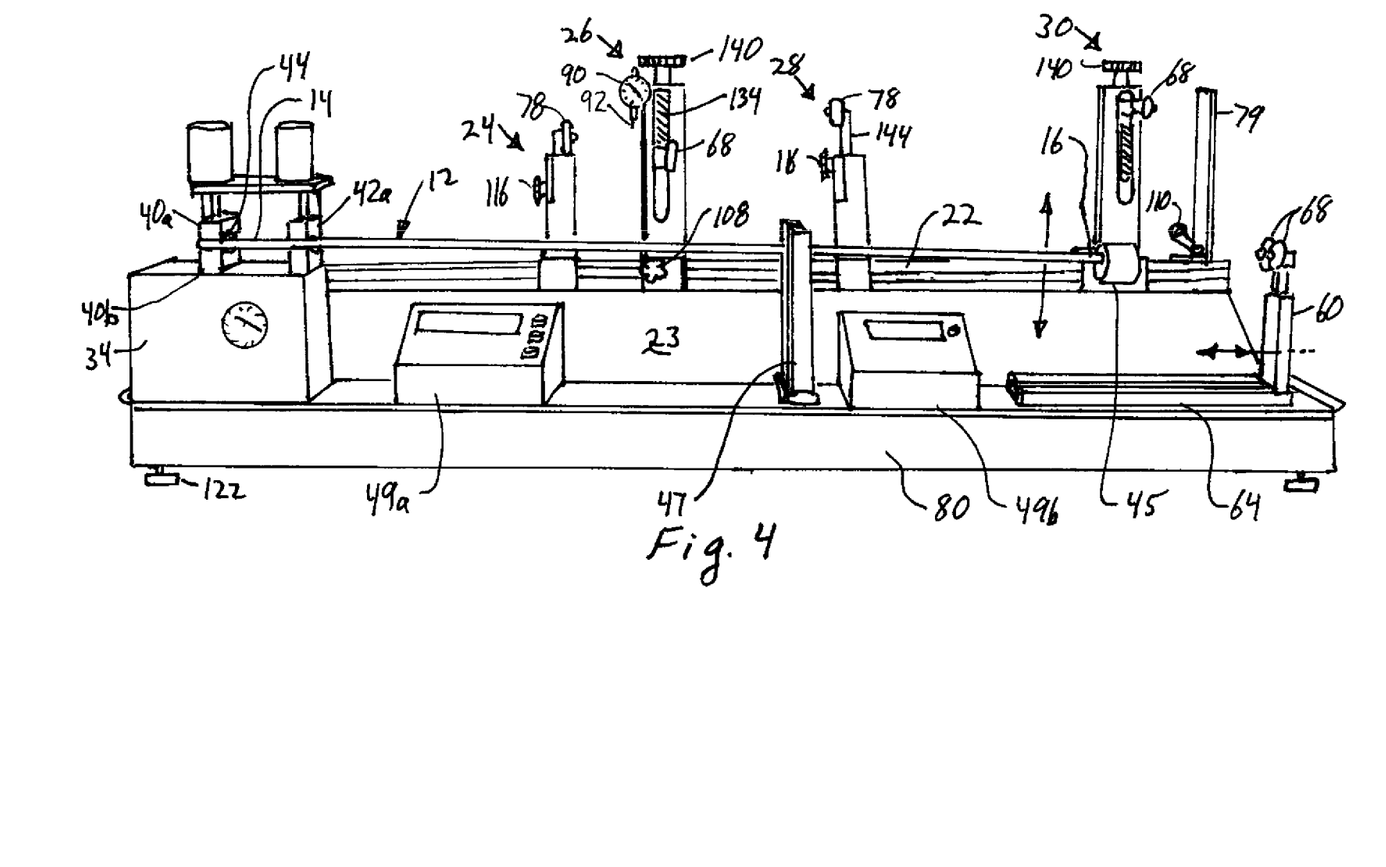
FIG. 4 shows a front perspective view of the testing station of FIG. 1 with a vibration testing apparatus and the towers changed from the arrangement shown in FIG. 1.

The station 10 has a lower portion 21 extending along a longitudinal axis that may be parallel to the longitudinal axis 18 of the shaft 10 during testing, but the base can take various shapes. The housing has a rail 22 supported above the lower portion 21 and fastened to a top housing portion 25. Four towers 24, 26, 28 and 30 are fastened to the rail 22 and preferably are fastened so the towers can move along the length of the rail 22 and may be fastened at various locations and in various orders or arrangements. The left and right towers shown in FIG. 4 are towers 24, 30, respectively, are located at the left and right ends of the rail 22 and lower portion 21 as seen in FIG. 4. FIG. 1-3 have the first and second towers 24, 26 in a reversed order. The term "middle towers" will be used to refer to whichever towers 24, 26, 28 or 30 are located between the end most left and right towers. The first and third towers 24 and 28 may have the same general construction and each preferably contains a force sensing device and a shaft positioned 68, 78 (described later) that provide support to the shaft while allowing the shaft to rotate about its axis. The positioners 68, 78 can take various forms, including V-shaped parts, but the positioners preferably comprises a pair of rollers. The force detectors or load sensors 74 in towers 24, 28 can detect forces along the vertical axis, both upwards and downwards, with the force detected by each load sensor being advantageously displayed by a display device 49. Separate display devices 49 can be used, or a common display device can be used. The towers 26, 30 have similar construction and each contains a set of rollers 68 vertically positionable by a lead screw.

The rollers 78 are like the rollers 68. The paired rollers 78 are mounted to rotate in the same plane which is orthogonal to the longitudinal axis 18 of shaft 12 during use. Advantageously the rotational axes of the rollers 78 are parallel to the longitudinal axis 18 and close enough that the outer periphery of each roller almost hits the adjacent roller. The rollers 78 advantageously have tapered cross-sectional profiles converging at a narrow rim at the periphery to provide a point support or a narrow line support of less than about 3 mm and preferably less than about 0.1 mm. Having described rollers 78, the rollers 68 are not further described. The rollers 68, 78 comprise shaft positioning devices which abut and position the shaft 12 while allowing the shaft to roll or twist relative to the positioning devices. While the paired rollers are preferred for this positioning device, other devices could be used, including suitable stiff rods with circular cross sections.

Each of the towers 24, 26, 28 and 30 has a base 32 configured to connect to the rail 22 and releasably fasten to the rail so as to resist movement along the rail and to support the tower fastened to the base in a fastened mode, and to allow movement in an unfastened mode. The base 30 also contains a releasable fastening mechanism that releasably holds the position of the towers 24, 26a, 26b and 28 on the rail 22. The base 32 and its connection mechanism are described later.

The test station housing 20 has lower portion 21 that is generally horizontal and that is joined to an inclined portion 23 joined to a top portion 25 that is generally horizontal and to which the rail 22 is fastened. A raised portion 34 at the left end of the lower portion 21 as seen in FIG. 1, with the raised portion 34 supporting a mechanism for holding shaft 12 during testing. One of the ends 14, 16 of the shaft 12 is inserted into and held by a releasable clamp mechanism 35 fastened to the raised portion 34. The clamp mechanism 35 has two pistons 36, 38 moving two upper clamp jaws 40a, 42a toward and away from two lower clamp jaws 40b, 42b. The lower clamp jaws 40b, 42b are mounted to the upper portion 34, and the upper clamp jaws 40a, 42b are connected to the pistons 36, 38, respectively. The pistons 36, 38, move the upper jaws 40a, 42a, towards and away from lower jaws 40b, 42b, respectively. Jaws 40, 42 may be actuated electronically, pneumatically, hydraulically or mechanically, with electronically actuated solenoid pistons being believed suitable for use.

The clamping jaws 40, 42 are spaced apart along a length of the shaft 12 and station 10, with outer clamping jaws 40 being at the left, outer end of the test station 10 as seen in FIG. 1, and the adjacent, inward or inner clamping jaws 42 located a few inches away toward the other end of the station 10. The depicted jaws 40, 42 may be generally rectangular in shape with a width along the length of the axis of about 2 cm and a length perpendicular to the axis and shaft 12 of about 5 cm. Advantageously, both parts of the jaws 40, 42 have a notch 44 to center and hold the round end 14 or 16 of the shaft 12. A notch 44 with an included angle of about 120° is believed usable, with the notch being wide enough to accommodate the diameter of the shafts 12. The notch may form a triangular opening with the apex of the triangle on an axis perpendicular to lower portion 21. Preferably, a notch 44 is placed in each of the clamp jaws 40a, 40b, 42a, 42b which face each other, with the apex of the notches 44 aligned on a common plane so the notches 44 center the axis 18 of shaft 12 along that plane. Thus, the shaft 12 rests in and is centered by the notches 44. Other configurations for the clamps can be used.

The clamp mechanism 35 holds the shaft 12 so the shaft extends along the length of the housing 20 and along the four towers 24, 26, 26, 30, with the upper portion 34 placing or raising the location of the clamping mechanism 35 to a predetermined height relative to these towers. The jaws 40, 42 are aligned so a centerline 18 of the shaft 12 is held along a predefined axis that is preferably, but optionally, horizontal.

A pair of sensor supports 46 extend from or are fastened to the lower portion 21 between the ends of the lower portion 21, and preferably past center toward the end away from support 34. Advantageously the sensor supports 46 are at a location that places the supports 46 between the two outer towers 24, 30. Sensors 47, such as photo-sensors, may be placed in the sensor supports 46, with the supports and sensors located so they extend along a portion of the shaft 12 when it is held in the clamp mechanism 35. The supports 46 are spaced far enough apart so they do not hit the shaft 12 when the shaft vibrates during testing.

Further adjustment to determine the shaft properties, as discussed in more detail below, is achieved by the adjustments and positionability of towers 24, 26, 28, 30. On towers 24, 28, the rollers 78 are fastened to a positionable bracket 77 mounted on the load cell 74. The positionable bracket 77 allows vertical adjustment and positioning of the paired rollers 78 relative to the load cell 74 and rails 22 or lower portion 21. This allows the rollers 78 to engage the bottom or top of the shaft 12. Moreover, the load cell 74 is cantilevered from side 75 so there is a gap between the load cell 74 and the base 76 which is fastened to the positionable fastening mechanism 32 on the rails 22.

Figure 5A:
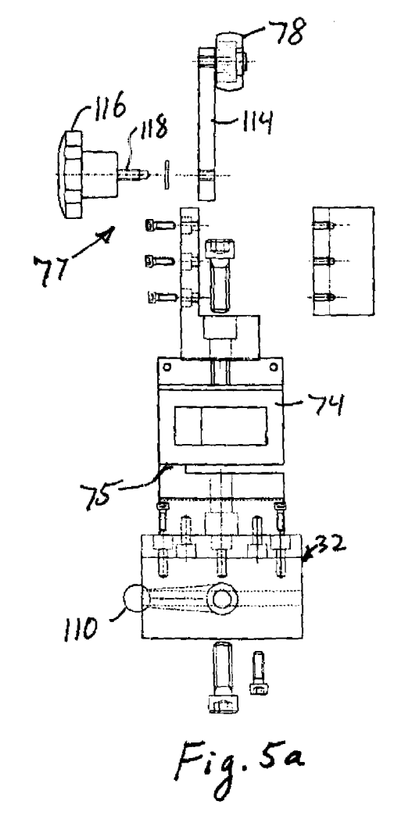
FIGS. 5a, 5b and 5c, show partially exploded front, end and top views, respectively, of a tower having a load cell and an adjustable shaft positioner.
Figure 5B:
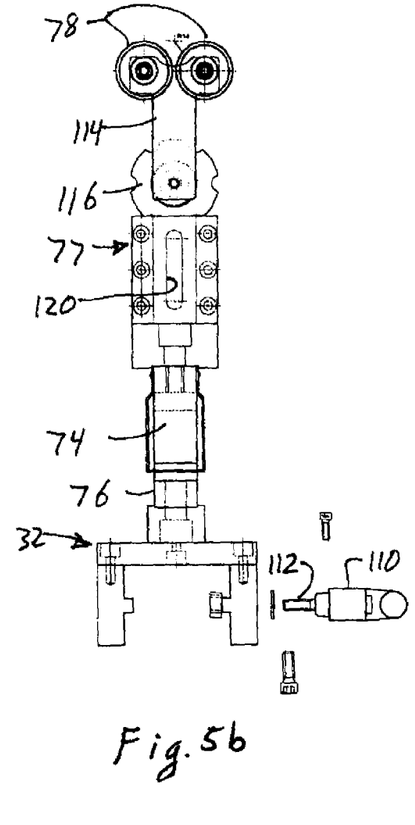
Figure 5C:
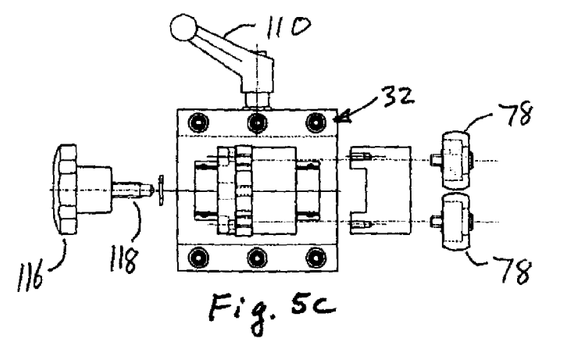

Stiffness: Referring to FIGS. 1, 4 and 5, a weight 45 is removable fastened to the free end 16 of the shaft 12. For discussion the gripping end 14 will be held in clamping mechanism 35. But it is understood that either end 14, 16 could be held in clamp mechanism 35 and in such cases the use of the test station 10 would proceed as described but with the position of the shaft 12 reversed. The weight 45 is clamped to the shaft by various means. The depicted mechanism has the weight 45 comprising a tool chuck with the jaws of the chuck tightened over the outside free end of the shaft 12. The end of the shaft 12 is butted against the internal end of the chuck and the chuck is tightened by hand to grip the shaft tight enough to hold the weight in place but without damaging the shaft or abrading the surface of the shaft. A chuck weighing between 1-4 pounds (is believed suitable, with a 2-3 pound chuck being preferred. The chuck allows the center of gravity of the chuck to be located beyond the free end of the shaft 12, providing more shaft deflection for a given weight than if the weight 45 were centered on the shaft itself. The chuck thus provides a cantilevered weight to provide additional shaft deflection.

In use a shaft 12 is held in jaws 40, 42 so the shaft extends between and beyond sensor supports 46, with the weight 45 on the end 16 of shaft 12 beyond the supports 46. The vertical deflection of the shaft 12 caused by the weight 45 can be measured and recorded and the location of the weight 45 along the length of the shaft and the distance from jaws 40, 42 determined and recorded. This can be done by taking a photographic image capturing the vertical displacement and weight location, which image(s) are later viewed on an electronic display or printed in order to measure the deflection electronically or manually. Images of the deflected and undeflected shafts may be used. Advantageously, only the deflected shaft position may be used if the shaft location is consistently when held by the jaws 40, 42 in the undeflected position. Further, by abutting the grip end or head end of the shaft against a wall or stop adjacent the jaws 40, 42, then shafts 12 may be consistently positioned and by knowing the shaft length and location of the jaws 40, 42, the location of the weight 45 on the shaft 12 may be determined by noting the location of the weight relative to the free end of the shaft.

The deflection can also be determined by fastening a vertical scale on the lower portion 21, on tower 28, 30, or on sensor supports 46 and visually monitoring the deflection relative to the scale. Alternatively, the sensors 47 could be configured to monitor vertical deflection electronically at the location of the shaft activating the sensors 47. Further, a tower such as tower 28, 30 could have a reference point fastened to it with a measurement device for measuring the vertical distance from the reference point to the shaft. Various mechanical measurement devices can be used, including a dial indicator and a scale. Various optical devices could be used, including laser optical devices, or image capture devices used alone or in combination with optical analysis and electronic analysis equipment and software.

The deflection can be determined with the shaft 12 in only one position, or the jaws 40, 42 can be loosened and the shaft rotated and the jaws re-clamped in order to check deflection along different cross-sectional axes of the shaft 12.

The shaft 12 also passes through the sensor range of sensors 47 positioned at a defined location along the length of the shaft. Sensors 47 comprising light emitting diodes on one support 46 and photo detectors on an opposing sensor supports 46 are preferred. Advantageously the sensors 47 are located relative to the jaws 40, 42 to put the sensors past the mid-point of the length of shaft 12, and advantageously between about 2-30 cm horizontally away from the distal tip of end 14 of shaft 12, and more preferably between about 2-10 cm horizontally. The distance of the sensors 47 from the grip end 14 will vary with the length of the shaft 12.

Bending Stiffness & Frequency: Referring to FIG. 4, the weight 45 is deflected vertically downward toward the lower portion 21a predetermined distance and released. The vibration frequency, amplitude and decay of the shaft 12 is detected and measured by the sensors 47, and preferably recorded. That information can be used to determine shaft bending stiffness. The amount of lateral or sideways oscillation of the shaft 12 (e.g., measured in the horizontal plane) can also reflect the uniformity of the bending stiffness of the shaft 12. As limiting criteria, the spacing between the sensor supports 26, centered on opposing sides of shaft 12, can be used to check that the lateral movement is less than a predetermined amount corresponding to the spacing from the shaft to the adjacent support 46. For example, if the shaft 12 oscillates under a vertical excitation force and hits a sensor support 46 when the supports are placed 8 cm apart, then the shaft is unacceptable. By varying the distance between supports 46, the amount of permitted lateral oscillation can be bounded. Alternatively, if the sensors 47 detect an unacceptable minimum or maximum deflection then an electronic signal may be generated resulting in a visual or audible signal to indicate such deflection.

Preferably, the base has a visual display mounted on the wall 23 to reflect the results of test data. Thus, the output of sensors 47 is preferably visually displayed on bending display 49a for fast evaluation by the operator. Various electronic circuitry and/or computer software can convert the signal from sensors 47 to various display formats for use by the computer and activation of the display 49a or suitable audio or visual alarms or indicators.

One exemplary way to determine the bending frequency for a shaft 12 with a weight 45 located a distance L from the clamps 42 as generally shown in FIG. 4, can be approximated by the following equation:

$$f=(1/2\pi)(3EI/ML^3)^{1/2}$$

Where
f=frequency (Hz or cps)
E=Young's Modulus (N/m² or lb/in²)
I=Area moment of inertia (m⁴ or in⁴)
M=weight at end of shaft (Kg or lbs.)
L=length of shaft from clamps 42 to weight W (m or in.)

Figure 9:
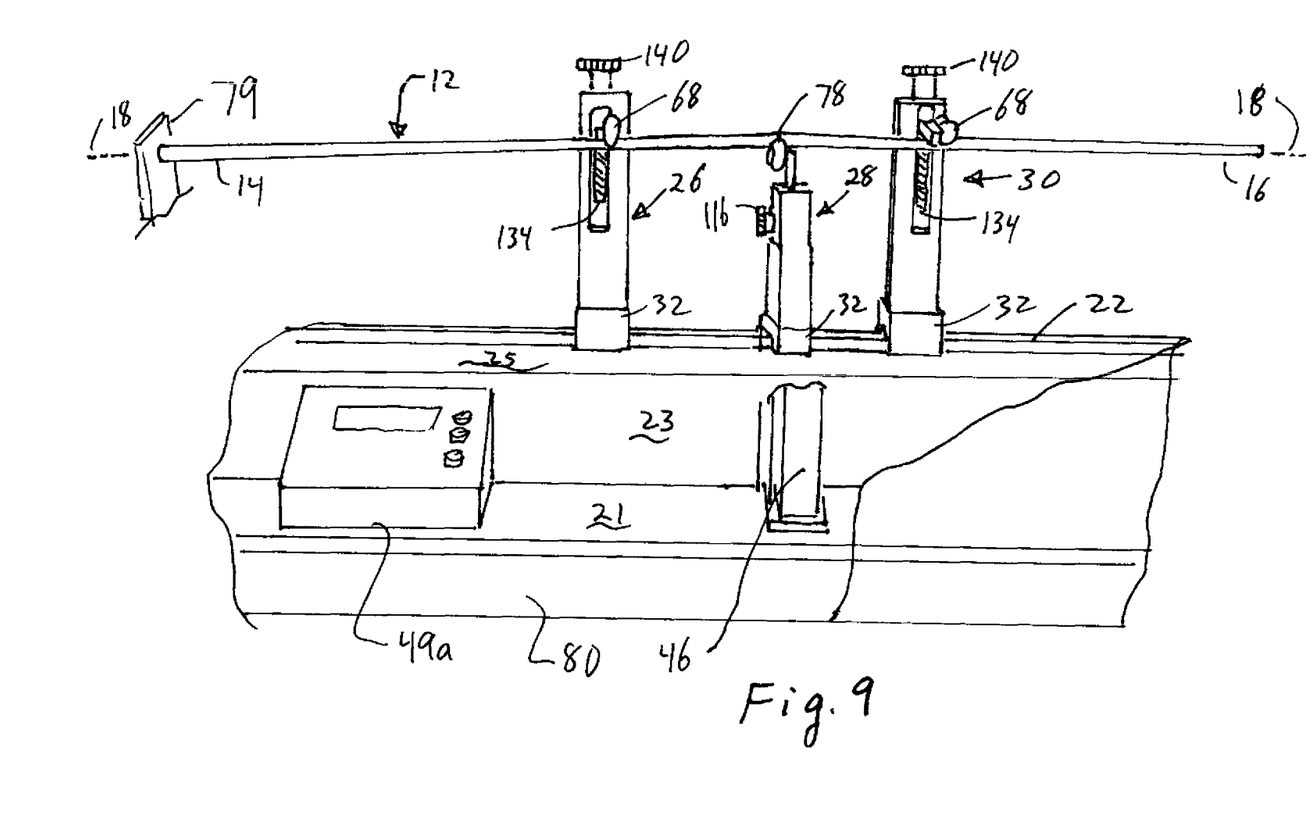
FIG. 9 is a perspective view of a portion of the test station of FIG. 4 configured for testing or checking shaft bending and shaft bending stiffness.

Bending Stiffness At Specific Location: By using towers 24, 28 with load sensors and one of towers 16, 30, further options are available for determining the shaft stiffness. Referring to FIG. 9, shaft 12 is placed with its grip end 14 abutting T-shaped mount 114 or 79 mounted to the rail 22. The third tower 28 is placed so its rollers 78 are spaced apart a known distance from the grip end of the shaft 12, and a linear scale (not shown) extending along rail 22 along top 25 can be used to adjust and position the tower location and location of its associated rollers 78, accordingly. The height of rollers 78 on tower 24, 28 are optionally adjusted so the longitudinal axis 18 of shaft 12 is substantially horizontal. The fourth tower 30 has its rollers 68 adjusted below the axis 18 and positioned to engage the shaft 12 and bend it a predetermined distance from the horizontal axis 18 of shaft 12. Thus, a user can manually grab the club end 16 of the shaft 12 and bend it down and below rollers 68 on tower 30. By knowing the location of the rollers on tower 30 and the vertical offset of those rollers from the axis 18, the amount of bend can be determined. The rollers 68, 78 can be positioned in various horizontal locations and vertical positions to achieve various bending configurations of the shaft 12.

For a spring the bending force F is equal to the stiffness times the deflection distance. Alternatively stated, bending stiffness is the force divided by the deflection. The load cells 74 in towers 24, 28 can determine the bending forces at those locations and thus allow determination of the shaft bending stiffness. An illustrative calculation is as follows:

Moreover, by rotating the shaft on rollers 68, 78 and watching the readout or force detected by load cells 74, the spine of the shaft can be located, at least for the location of tower 28. Since the towers 24, 26, 28 and 30 and their associated rollers 68, 78 are positionable, the stiffness and spine at various locations can be determined.

While the above description fastens uses the first tower 26 to hold one end of the shaft 12, the end of the shaft 12 could abut the stop 79, with the shaft bent over the rollers 78 of the tower 28 and held in a bent position by rollers 68 of tower 26. The rollers of tower 30 are lowered to avoid interference with the shaft bending. Thus, either of the towers 24, 26 and their associated load cells 74 could be used to determine this bending stiffness discussed above. There is thus provided an improved way to determine bending stiffness and spine in a multi-function test station. For example, the bending stiffness for shaft 12 with spaced apart rollers 68 on the top of the shaft 12 and rollers 78 beneath the shaft and between rollers 68, as shown in FIG. 9, is approximated by the following equation:

$$EI_a=(Ra_1a_2)^3/(3.13(a_2-a_1)\delta)$$

Where:
E=Young's Modulus (N/m² or lb/in²) I=Area moment of inertia (m⁴ or in⁴)
R=force (g or lbs) measured by load cell in the applicable tower 24, 28 located between towers 16, 30 (illustrated as tower 28 in FIG. 9)
$a_1$=the distance between rollers 68 on tower 26 and rollers 78 on tower 28 (m or in.)
$a_2$=the distance between rollers 78 on tower 28 and rollers 78 on tower 30 (m or in.)
δ=The deflection at rollers 78 from the centerline 13 of the shaft 12 ((m or in.)

Figures 7A, 8A:
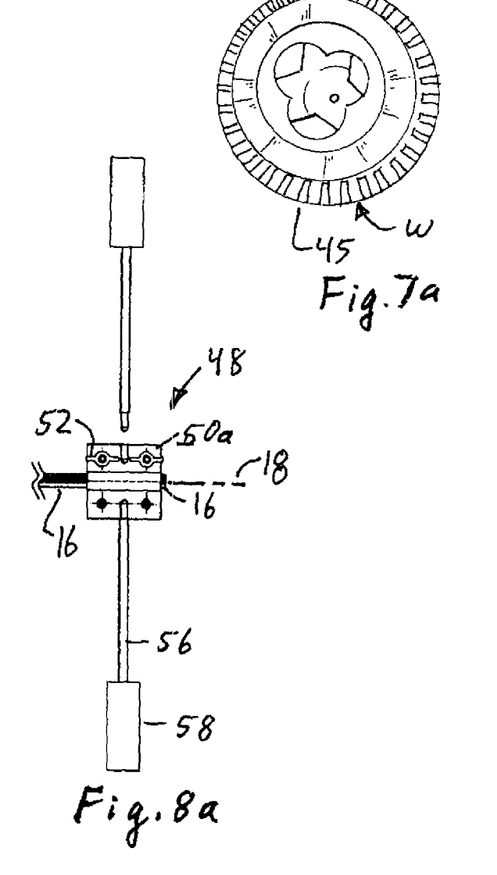
FIGS. 7a, 7b show a front and side view of a tool chuck, respectively.
FIGS. 8a, 8b and 8c show the top, front and end views, respectively, of a torsion assembly on the end of a shaft.
Figure 7B:
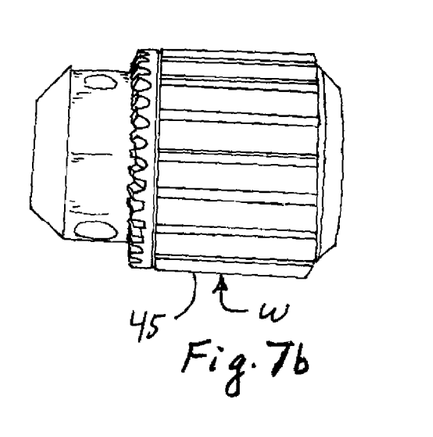
Figure 8B:
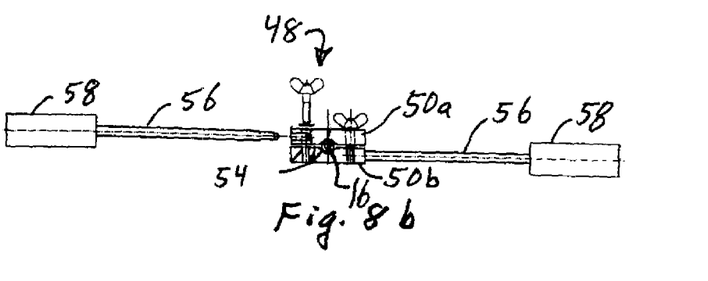
Figure 8C:
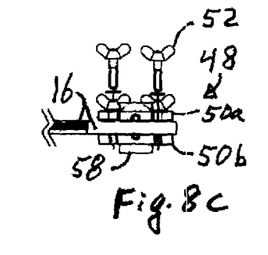

Torsional Testing: Referring to FIGS. 2-3 and 8 a torsional weight assembly 48 is fastened to the free end 14, 16 of the shaft 12 and rotated to measure the torsional resistance and vibration period of the shaft using the sensors 48. The torsional assembly is shown in broken lines in FIG. 2. For ease of explanation head end 16 will be used here but the test could be conducted with either end. The torsional weight 48 has a mounting bracket 50 shown as composed of two plates 50a, 50b fastened together by thumbscrews 52. A notch 54 is formed in the surfaces of the plates 50a, 50b which face each other, with the notch sized to accept one end 14, 16 of shaft 12. From opposing sides of one of the plates 50, a shaft 56 connected to one or more counterweight(s) 58 extend. The shafts 56 and counterweights 58 may be centered along a common axis, or offset as in FIG. 8. The torsional counterweights 58 are offset from the longitudinal axis of shaft 12 in order to significantly increase the rotational inertia compared to the chuck or weight 45 used for vibration frequency testing.

In use, one end 14, 16 is placed in the notch 54 and the plates 50a, 50b tightened by thumbscrews 52 to clamp an end 14, 16 of the shaft 12. The assembly of plates 50, thumbscrews 52, shaft 56 and counterweight 58 is balanced to have a defined inertia centered about axis 18 of shaft 12 which extends through or very close to the center of gravity of the torsion assembly 48. As described later, rollers 68 abut the shaft 12 adjacent the torsional assembly 48 to support the shaft while allowing free twisting of the shaft 12 under torsional load and oscillation. When the torsion assembly 48 is rotated and released, it causes shaft 12 to rotate or twist about longitudinal axis 18 as best shown in FIG. 3. The sensors 47 monitor the vertical and lateral shaft motion—especially when the shaft is unrestrained.

Referring to FIGS. 1-3, in order to limit lateral movement under torsional testing, an end support 60 is preferably used to support the end 14, 16 of shaft 12 during torsional testing. End support 60 may have a movable base 62 mounted to travel along tracks 64 fastened to the lower portion 21 (FIG. 3). A clamp mechanism, latch mechanism, screws or thumbscrews fasten the end support 60 in a desired position which may be changed depending on the length of the shaft 12. A vertical support 60 extends from the base 62 with a pair of laterally spaced rollers 68 on its distal end. The shaft 12 rests between the rollers 68. The rollers 68 are on opposing sides of the shaft 12 with their rotational axis aligned with the longitudinal axis 18 of the shaft 12. The longitudinal position along the length of lower portion 21 can be varied by moving the base 62 and support 60 along tracks 64, in order to support the shaft 12 at various positions along the length of the shaft, or to accommodate shafts 12 of differing length.

For testing a torsional force is applied to the shaft 12 by the torsion weight 48. The torsional force may be applied various ways. Advantageously a wedge shaped plug is inserted into the end of the tubular shaft 12 to engage and rotate the shaft. The plug can have a rotational clutch that releases at a predetermined torque. An engaging mechanism could be configured to engage the plates 50 or the shafts 46 or other portions of the torsion assembly 48. Alternatively, one of the counterweights 58 can be deflected downward toward lower portion 21 a predetermined amount and then released to place the shaft 12 in torsion. As seen in FIG. 3, rotation of the shaft and counterweights 58 causes the counterweights 58 to move in a circular motion. The shaft 12 is preferably supported so the counterweight motion is limited to avoid the counterweights 58 hitting things. The wall 20 is advantageously inclined to accommodate the rotation of shaft 12 and counterweights 58.

When the shaft 12 is twisted and vibrated by torsion assembly 48, a torsional sensor 70 measures the frequency of rotation of counterweights 58. The torsional sensor 70 may be mounted to the rail 22 and is preferably movably mounted along the length of the rail 22 to accommodate shafts 12 of differing length. The sensor 70 is preferably an optical sensor that reflects light off a counterweight 58 and detects that light to measure the frequency. If a reflective sensor is used, then the end of counterweight 58 adjacent the sensor 70 advantageously has a reflective surface on it. The sensor 70 could be a proximity sensor, or other type of sensor.

The rate of torsional decay can be used to calculate and test the radial and/or torsional stiffness of the shaft 12. A torsional display 49b can optionally display the results either in terms of a measurement of frequency, a measurement of the torsional stiffness, a sinusoidal signal showing the amount and frequency of deflection and decay, or it may display the information in other formats. To help prevent confusion, a separate display 49b is preferably used for displaying torsional testing information. Thus, a display 49a is used for bending frequency and/or stiffness, and a display 49b for torsional frequency and/or stiffness. A single display could be used, but to avoid confusion separate displays are preferred. The data from sensors may be processed by suitable electronics, microprocessors or software to make the data suitable for display 49b. The processing means are generically referred to as and encompassed by the term computer processors.

For example, the torsional frequency for a shaft 12 with offset weights 58 located a distance L from the center of the shaft, as generally shown in FIGS. 2 and 3, can be approximated by the following equation:

$$f=(30/\pi)(G_a I_p g/TL)^{1/2}$$

Where
f=frequency (Hz or cps)
$G_a$=Average shear modules of shaft (N/m² or lb/in²)
$I_p$=Area moment of inertia (m⁴ or in⁴)
g=gravity acceleration (9.81 m/s² or 32.174 ft/s²)
T=torsional moment on shaft (Kg-m or in-lbs.)
L=length of shaft from clamps 42 to clamp 50 (m or in.)

Balance Point: The balance point is the center of gravity of the shaft 12, and if the head 17 is attached may represent the center of gravity of the entire golf club. For illustration, the shaft alone is used in the following explanation. Since the shaft is tapered, the balance point is not the middle of the shaft. To determine the balance point, the operator rests the shaft 12 on one pair of rollers 78 on towers 24, 28 and slides the shaft over the rollers until the shaft balance point is located and visually marked on the shaft. The tower 28 is especially useful for this task because the rollers 68 on adjacent towers 26, 20 can limit the amount of tilting which can occur when the shaft rests on the rollers 78. When the shaft 12 is horizontal the balance point is on the rollers 78, that point is marked with tape, chalk, marker or other visible indicia. When the shaft 12 is balanced so it does not tip and slide off the rollers 78, the balance point may be checked against a linear scale on the rail 22 or top 25 to confirm the balance location is within acceptable parameters. By butting one end of the shaft 12 against end stop 79 and then moving it slightly away to reduce frictional contact, and then positioning the scale relative to the stop 79, the location of the balance point can be consistently evaluated to ensure it falls within acceptable limits. For shafts of the same length balanced on the same rollers 78 of 28, the rollers should always be within a similar distance of the stop 79 when the end of the shaft is adjacent the stop 79. Further, one or more lines along the length of the rail 22 or wall 23, or structures extending in straight lines along those parts can be used to visually align the shaft to these lines in order to assist in determining the balance point.

Note that when the shaft 12 is balanced on rollers 78, the entire weight of the shaft is measured by the load cell 74 on tower 28 (or 24), thus also determining the weight of the shaft 12. Towers 24, 28 could be used to determine the balance point but they are not preferred since they lack the load sensor and cannot determine the weight using that sensor 74.

One additional method of determining the balance point is available since the test station 10 has two load cells 74. The grip end of the shaft 12 can be butted against the T-shaped mount 114 so the grip end is below the rollers 78 on the first tower 24. The rollers 78 on the third tower 28 can be positioned below the shaft 12 and to the left of the anticipated balance point. As needed, end stop 79 may be rotated out of the way to prevent contacting the shaft 12 or club head. By measuring the distance between the rollers 78 and using the forces from each load cell 74 below the rollers 78 on towers 24, 28, the center of gravity or balance point can be calculated by balancing the vertical forces and moments using the weight of the shaft (or club). A scale on the top housing portion 25 along the rail 22 can be used to readily determine the distance between rollers 78 because the towers 24, 28 are constructed the same. Alternatively, the tower 28 can be moved laterally until the force on the load cell 74 of tower 24 reads zero, with all of the club or shaft weight on the rollers 78 of tower 28 to locate the center of gravity or balance point. This requires that the tower 28 not be too high relative to the first tower 24, but one skilled in the art can adjust the height appropriately.

Figure 11:
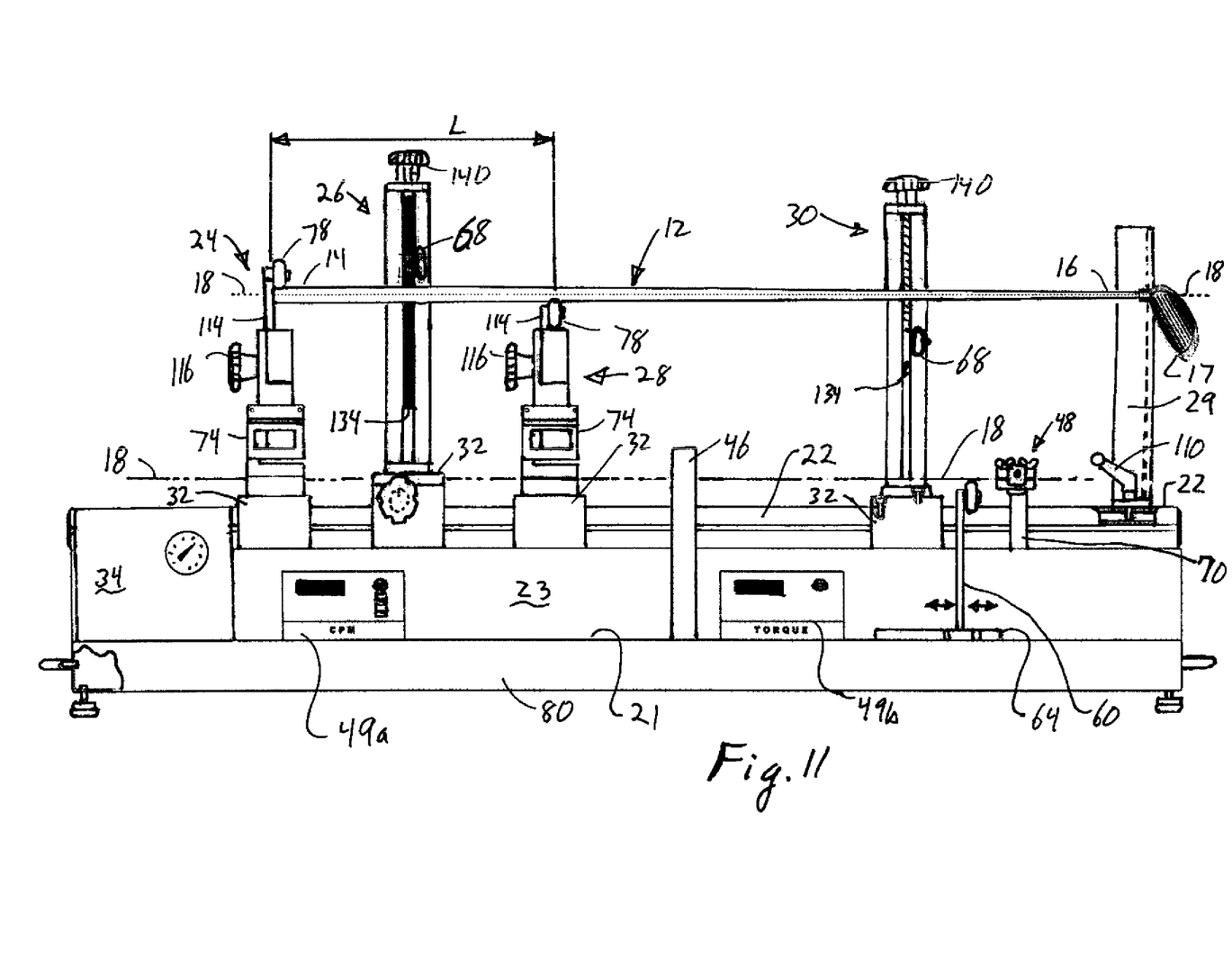
FIG. 11 is a front plan view of the test station of FIG. 4 configured for determining swing weight.

In particular, and referring to FIG. 11, the load cells 74 on towers 24, 28 can measure the force or weight exerted by the club on the rollers 78 and their associated load cells 74 to determine the club weight and balance point. The club weight or shaft weight is determined by the formula:

$$W_{club} = F2 + F1$$

Where $W_{club}$ is the weight of the club (or shaft if head 17 is absent), F2 is the force on rollers 78 on tower 28 measured by the associated load cell 74, and F1 is the force on rollers 78 on tower 24 measured by load cell 74 of that tower.

The location of the Center of Gravity (CG) or balance point from the grip end 14, is determined by the formula, when the rollers 78 on tower 28 are located 14 inches from the grip end 14 of the shaft. If a distance other than 14 inches is used, the formula is modified accordingly:

$$L_{CG} = 14 \times (F2)/(F2-F1)$$

Thus, by using tower 24, 28, each with a load cell 74, determining the balance point can also determine the shaft weight or club weight. If the head is attached during the measurements, the center of gravity will shift toward the head, but the method and use of the apparatus as described above remains the same.

Swing Weight:

The swing weight reflects how the weight of a golf club feels when it is swung. The swing weight is a function of the distance between the balance point (center of gravity) of a club and a point usually 14 inches from the grip end 14 of the shaft. Sometimes a 12 inch dimension is used for the swing weight of the 14 inch swing weight dimension. Since shafts 12 are tapered, the center of gravity is not the middle of the shaft, thus determining the swing weight is not straightforward.

Referring again to FIG. 11, the same setup is used as for determining the weight and CG, by placing a shaft 12 with its grip end 14 abutting T-shaped mount 114 below rollers 78 on tower 24. The third tower 28 is placed so its rollers 78 are 14 inches from the end of the shaft 12 (or 12 inches if a 12 inch swing weight is used). The stop 79 is moved out of the way as needed to avoid hitting the shaft 12 or head. Thus, the shaft 12 has the grip end 14 below rollers 78 on tower 24 and the rollers 78 on tower 28 below the shaft so that the shaft is supported by towers 24, 28. Both rollers 78 are to the left of the center of gravity of the club. The load cells 74 on towers 24, 28 measure the force or weight exerted by the club on the rollers 78 and load cells 74.

By locating the rollers 78 of tower 28 below the shaft 12, and locating those rollers 78 the swing distance (14 inches) away from the grip end 14, the force measured by the load cell 74 on tower 24 reflects the weight needed to balance the club about the rollers 78 on tower 28. That balancing weight reflects the swing weight. The scale on top 25 can be used to locate tower 28 and its rollers 78. The tower 28 can be positioned to use whatever swing weight distance is desired. The swing weight designation is an alphanumeric compilation of letters and numbers where letters range from A through G, and numbers 0 through 10. A0 is the lightest and G10 the heaviest. Men's clubs are typically in the D0 or D1 range and women's clubs in the C5 to C7 range. Exemplary distances correlating the swing weights with the distances between the location 14 inches from the grip end and the center of gravity are given in Table I.

For a 14 inch swing weight, where the distance between rollers 78 is 14 inches, the swing weight is $0.0897F_1$, where $F_1$ is the reading in grams of load sensor load sensor 74 on tower 24 as shown in FIG. 11. This swing weight corresponds to the swing weight determined using a standard 14 inch swing weight system with a standard movable balance weight $W_0$. A more generic formulation is that the swing weight is $14F_1/W_0$. One skilled in the art could determine other conversion equations to use the load values of sensors 74 to determine swing weights based on distances other than 14 inches from the grip end.

Figure 10:
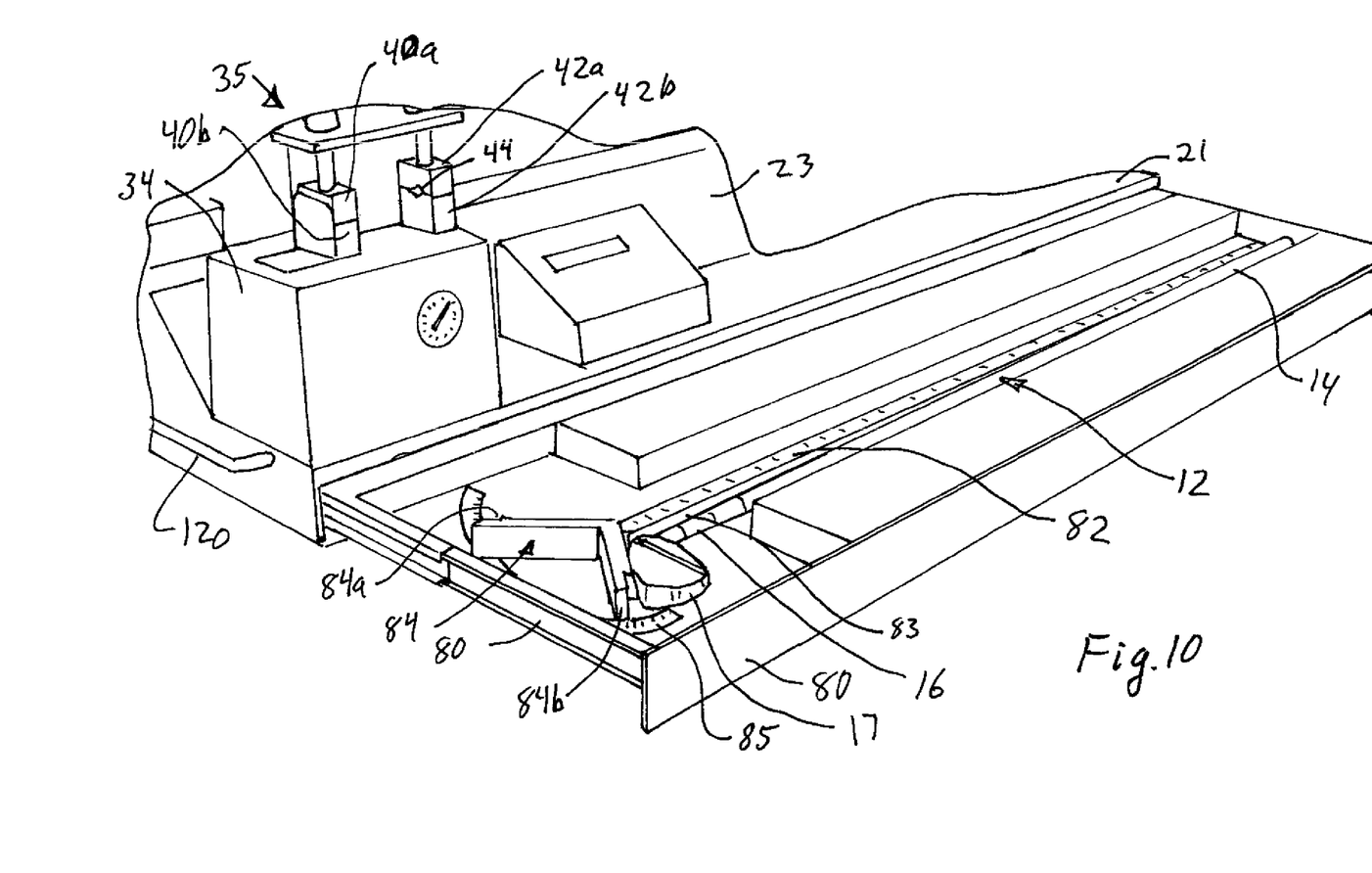
FIG. 10 is a perspective view of a portion of the test station of FIG. 1 with a drawer pulled out.

Club Length: Referring to FIG. 10, a shelf or drawer 80 slides into and out of an opening in the lower portion 21. The shelf 80 has a linear scale 82 extending along a length of the drawer. The scale 82 is preferably located on a raised wall 83 about one inch high or smaller. The linear scale 82 could be on the bottom of the shelf 80 with pins replacing the wall 83. One or two end stops 84 are located at one end of the scale 82, illustrated here as the left end as viewed in FIG. 10. The end stop stops 84 preferably comprise pivotally mounted walls rotating about the center of a curved scale 85 marked to reflect angles like a protractor with the pivot point at the center of the protractor. The walls 84a, 84b can be independently rotated, but are preferably joined together at right angles with the pivot point located at the juncture of the walls 84 and also located at the center of the protractor scale 85. The linear scale 82 begins at the pivot point and extends along the (optional) raised wall 83.

In use a shaft 12 fits along and is positioned by the wall 83 fitting with shaft 12 extending along the scale 82 and wall 83 so the head end 16 is adjacent end stops 84. The end stops 84 rotate to align with the angle of the club head when the shaft is against the wall 83. The club length is measured with a golf club head fastened to the head end 16 of shaft 12. One end stop 84a is used for right handed golf clubs and the other end stop 84b is used for left handed golf clubs. The club head abuts one of the end stop 84a, 84b and the positioning mechanism 83 position the club for accurate measurement of the club length using linear scale 82, while the curved scale 85 shows the angle of the bottom of the club head relative to the length of the shaft to determine the lie angle of the head Both the club length and head angle can be recorded and checked to ensure they are within specifications.

When not in use the shelf or drawer 80 can be pushed into lower portion 21, which has internal tracks and/or rollers to receive and support the shelf for storage inside the base. The storage inside lower portion 21 protects the scales 82, 85 and allows for a compact unit. Advantageously, the drawer 80 has raised foam inserts so the scale 82, wall 83, stops 84 and curved scale 85 are recessed relative to the foam inserts to protect those parts and to further help position the clubs and shafts during use of the scales 82, 85.

Optionally, the drawer may be configured to hold parts used for the various tests, including holding the weight 45 (e.g., a chuck), or the torsion mechanism. Advantageously, cutouts in the foam may be configured to the shape of these parts to retain them from movement during transportation of the test station 10.

Shaft Straightness: Referring to FIGS. 1 and 4, the shaft straightness is checked using any two of the four towers 24, 26, 28 or 30, as long as the towers are positioned so the center of gravity of the shaft 12 is between any of the two towers that are used in order to prevent the shaft 12 from falling off the towers. For illustration towers 26 and 28 will be used to support the shaft 12. The free end 16 of shaft 12 is supported on rollers 78 of tower 26 and rollers 68 of tower 28. The end 16 is butted against stop 79 to ensure consistent positioning and testing. The height of the rollers 68, 78 is adjusted to place them in a horizontal plane. The stop 79 can be positioned at either end of the rail 22. Height locations can be pre-marked on the towers to make this alignment faster. This places the shaft 12 along a straight line that is parallel to the rails 22 since the paired rollers 68, 78 on towers 24, 26, 28 and 30 are aligned in a common vertical plane.

The first or left tower 24 has a distance measurement instrument 90 accurate to fractions of an inch (e.g., 0.001 inches) or fractions of a centimeter or millimeter. While non-contacting optical instruments can be used which use emitted and reflected light to measure distances between objects, preferably the distance measurement instrument 90 is a dial indicator using either mechanical instruments to activate the gauge or electronic instrumentation (usually load cells, strain gauges or piezoelectric devices) to activate the gauge. The instrument 90 has a detector 92 which is positioned against the outer or exterior surface of the shaft 12 at the grip end 14. The tower 24 and distance measuring instrument 90 are then moved along the length of rail 22 while the straightness of the outer surface of shaft 12 is checked by movement of detector 92 along that surface. The movement of detector 92 can be recorded, visually displayed on gauge 94 or other display, or both. A straightness requirement of 0.005 inches is usually sought but the criteria can vary. Thus, since the shaft 12 is tapered, a linear increase is expected and that linear increase should not exceed 0.005 inches or whatever other criteria is selected.

Since the towers 24 and 26 are mounted on the same rail 22, the measurement instrument 90 on tower 24 cannot pass tower 26 and measure along the entire length of the shaft 12. The shaft 12 must thus be rotated end-for-end 180° so that the opposing end abuts the stop 79 to allow the instrument 90 to measure the remainder of the shaft 12.

After the length of shaft 12 is checked with detector 92, the shaft 12 can be rotated with the detector 92 traversing a circumference of the shaft to check for roundness at various locations of the shaft. Again, the movement of detector 92 can be recorded, visually displayed on gauge 94 or other display, or both. The notches 44 in jaws 40, 42 and the paired rollers 68 allow easy rotation of shaft 12 while maintaining the position and alignment of the shaft. In addition to testing for local roundness, the rotation allows checking for gross-bowing of the shaft 12 and allows checking for non-linearity of the shaft 12. The testing station 10 allows shaft 12 to be maintained in position for this test, thus increasing the accuracy of the testing and the speed with which testing is performed.

Shaft Spine: This test identifies any stiff side of the shaft 12 so that stiff side can be oriented relative to the head to achieve a desired performance. A spine oriented in a plane of the predicted ball trajectory as the ball leaves the club head is believed preferable, with the spine oriented toward the player. The spine is determined by rotating the shaft 12 under a predetermined load and measuring the deflection. The test procedure is similar to that used in the shaft straightness test, except that a weight is fixed to one end of the shaft 12, typically to the club head end 16. The chuck described above (FIG. 5) may be used to releasably attach a desired weight 45 to the shaft 12 for this test. The location of the spine on the shaft 12 can be marked on the shaft by chalk, marker, tape, or other means.

Kick Point: A low kick or bend point point is more flexible and can impart a high trajectory to a ball while a high kick point is stiffer and imparts a lower trajectory. The kick point reflects the location at which a shaft bends under axial loads. Because shafts 12 are tapered, the kick point or bend point is adjacent the narrower head end 16. The kick point using test station 10 is determined differently. The shaft 12 is placed below the rollers 68 on the towers 24, 28, and on top of the rollers 78 on tower 26, with the tower rollers 78 being high enough to bend the shaft 12. The shaft 12 is abutted against stop 79 for consistent results. The shaft 12 is then rotated end for end so that if the grip end 14 was abutting the stop 79 before the rotation then after the rotation the head end 16 abuts the stop. The load cell 74 measures the force for each deflection. The ratio of the forces measured by the load cells can be used to determine the kick point as measured relative to the head end 16 of the shaft 12.

Details of Construction: Referring to 3, 5 and 6, the towers 24, 26, 28 and 30 connect to the rails through fastening mechanisms 32. The rails 22 can comprise a single part or multiple rails. As seen best in FIG. 6c, the rail 22 advantageously comprises a single elongated part having a generally square cross section with a top surface having a longitudinal slot forming two separate rails 22a, 22b, with a gap or space between them. The sides also each have a slot 102a, 102b along the length of the rail 22. The fastening mechanisms 32 are configured to enclose at least two and preferably three sides of the rail 22. Guide pins or rollers 204a, 204b extend from opposing sides of the fastening mechanism and are located to extend into the slots 102a, 102b. The rollers 104 are guided along the rail 22 by slot 104. The rollers 104 preferably have a close fit in the slots 102 to more accurately position the towers 24, 26, 28 and 30. Advantageously, at least a pair of rollers is provided on each side of the rail 22 for each tower 24, 26, 28 and 30.

A shaft 106 with a gripping knob 108 at one end and threads at the other end is rotated to clamp the fastening mechanism to the rail 22. The shaft 106 can be manually rotated inward until it abuts the rail 22 to form a friction stop. Alternatively, shaft 106 can extend across the top of the rail 22 to engage a threaded surface on the opposite side of rail 22 so that rotation of the shaft draws the opposing sides of the fastening mechanism together to clamp against the rail 22 as shown in the left most tower in FIGS. 1 and 2. The knobs 108 rotate shafts 106 to allow positioning of the towers 24, 26, 28 and 30 and are tightened to clamp the towers in position relative to the rails 22. This provides a fast manual positioning mechanism to move the towers along the rails to desired positions. While the mechanism 32 provides a quick release connection to releasably fasten the towers 24, 26, 28, 30 to the rail 22, other quick release mechanism could be used, including cams actuated by levers to frictionally engage the rail 22 or top 25, or threaded fasteners engaging the rail 22 or top 25. Manually actuated connectors are preferred.

Referring to FIGS. 1, 2 and 11, the end stop 79 has a vertical extending stop portion connected to a laterally extending base that extends parallel to the rails 22. A handle 110 resembling a window crank is connected to a threaded shaft 112 that passes through a threaded hole in the base of the stop 79 to abut the rail 22 to fasten the stop 79 in position relative to the rail 22. Various handles or knobs can be used to tighten the stop 79 and clamps 32 in position. Preferably, the shaft 112 rotated by handle 110 extends into the slot between the rails 22 so that rotation of the handle 110 engages or disengages the end of the shaft 112 with the rail to fasten the stop 79 in position. The shaft 112 is offset from the plane of the stop 79, so that by loosening the handle 110 the stop 79 can be rotated 90° to move the stop 79 out of the path of a shaft resting on the rollers 68, 78. That also allows the stop 79 to be releasably positioned along the rails 22.

The handle 110 and shaft 112 could be used instead of the knob 108 and shaft 106, and such fastening mechanisms are shown on towers 26, 28, with the shaft 112 being shown in FIG. 5b.

Referring further to FIGS. 5a-5c, the rollers 78 are vertically adjustable relative to towers 22, 28 and rails 22. The rollers 78 are mounted on opposing ends of the cross-bar on a T shaped mount 114, with the leg of the T-shaped mount fitting into a recess formed by walls on the tower 24 (and 28). A knob 116 has a threaded shaft 118 that passes through a threaded hole in a wall of the recess to abut the leg of the T-shaped mount 114 to push against that mount and hold it in position. The shaft 118 can move upward and downward in a slot 120 in a wall forming the recess. By loosening and tightening the shaft 118, the position of the rollers 78 can be adjusted vertically, along the length of the tower 24 (and 28), and perpendicular to the rails 22.

The testing station 10 is portable and handles 120 on opposing ends may be optionally provided for moving the station. As used here, portable means light enough for two average males to carry. It is possible for one strong person to carry the test station 10, but not desirable. The test station also may have adjustable feet 112. Elastomeric bumpers fastened to threaded shafts engaging threaded holes in the lower portion 21 may provide suitable adjustment to keep the rails 22 and other axes horizontal during testing.

Figures 6A, 6B, 6C:
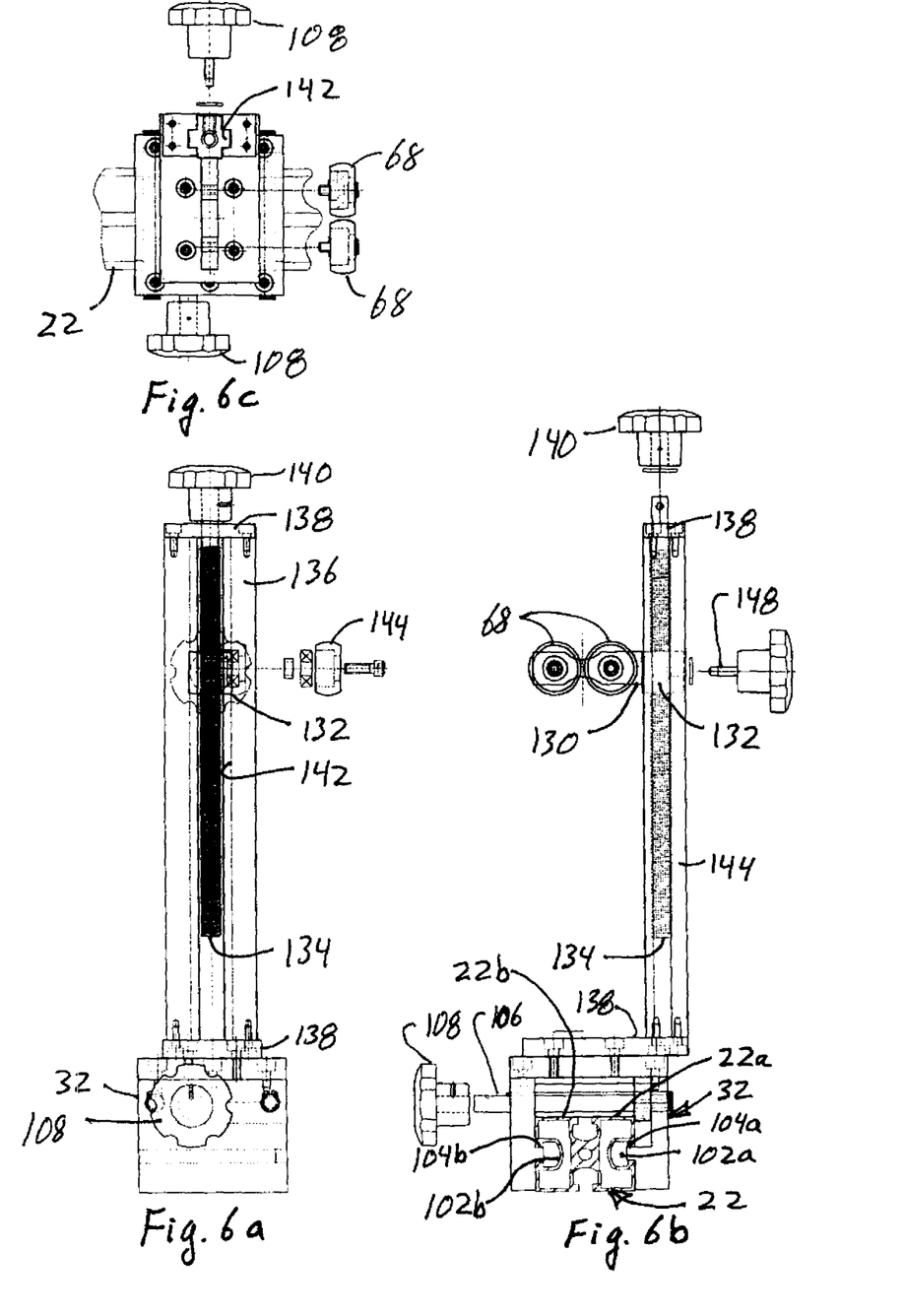
FIGS. 6a, 6b and 6c show partially exploded front, end and top views, respectively, of a tower having a laterally extending shaft positioned.

Referring to FIGS. 6a to 6c, the second and fourth towers 26, 30 have similar construction, including the fastening mechanism 32 previously described. The rollers 68 on each tower 26, 30 extend laterally from an elongated lateral mount 130 which has the rollers 68 on one end and may have a lead screw nut 132 on the other end. The rollers 68 are preferably constructed like rollers 78. The lead screw nut 132 has a vertical opening through which passes lead screw 134 which is vertically mounted by a bracket 136 having upper and lower end flanges 138 that extend to receive the ends of the lead screw 134. A knob 140 is connected to the top end of the lead screw 134, preferably with the lead screw passing through a hole in the upper end flange 138. The nut 132 has an elongated body or portion of its body passing through a vertical slot 142 (FIG. 6a) along the length of bracket 136. The slot 142 may be cut into the body of the bracket 136, or the slot may be formed by spaced apart, parallel ribs. Rotation of the knob 140 rotates lead screw 134. Because the body of nut 132 engages the sides of the slot 142, the nut and rollers 68 cannot rotate with the screw 134 and thus the nut 132, mount 130 and rollers 68 translate along the length of the lead screw 134. Preferably, a guide 144 is fastened to the body of the nut 132 with the guide 144 being oriented to roll or slide in the slot 142 to prevent rotation of the nut 132 and mount 130. As seen best in FIG. 6b, the slot 142 has a cross-sectional shape resembling a plus sign.

The rollers 68 on towers 26, 30 and rollers 78 on towers 24, 28 may thus be readily adjusted in vertical position. Advantageously, a scale is placed vertically along the towers or painted onto the towers to provide a readily accessible and easily viewable reference to help the user adjust the rollers 68, 78 to a desired height.

It is important that the test station 10 be stable and not move or flex easily during use. The angled shape of the inclined wall 23 relative to lower and upper portions 21, 25, with the top 25 strengthened by the rails 22 helps provide a rigid structure with sufficient stability that measurements of under 0.001 inch can be repeatedly made without distortion from movement or deflection of the test station 10. Making the towers 24, 26, 28 and 30 of metal rather than plastic is also believed desirable in order to increase the accuracy with which the parts of the test station are positioned and the accuracy with which the shaft 12 is positioned and tested.

Referring to FIG. 6c, a knob 146 with a threaded shaft 148 may passes through the bracket 136 with the end of the shaft 148 abutting the nut 134 or lead screw 134. Tightening or loosening the knob 146 and shaft 148 tightens or loosens the position of the rollers 68 relative to tower 24, 28.

The above description is given by way of example, and not limitation. Given the above disclosure, one skilled in the art could devise variations that are within the scope and spirit of the invention disclosed herein, including various ways of releasably fastening the towers to the rails, and various ways of configuring the rails and moving the towers along the rails. Further, the various features of the embodiments disclosed herein can be used alone, or in varying combinations with each other and are not intended to be limited to the specific combination described herein. Thus, the scope of the claims is not to be limited by the illustrated embodiments unless otherwise indicated.

TABLE 1

| S/W | F 1 (S/W Range) |
|---|---|
| B0 | 327.0~330.2 mm |
| B1 | 330.2~333.3 mm |
| B2 | 333.3~336.5 mm |
| B3 | 336.5~339.5 mm |
| B4 | 339.6~342.8 mm |
| B5 | 342.8~345.9 mm |
| B6 | 345.9~349.1 mm |
| B7 | 349.1~352.2 mm |
| B8 | 352.2~355.4 mm |
| B9 | 355.4~358.5 mm |
| C0 | 358.5~361.7 mm |
| C1 | 361.7~364.8 mm |
| C2 | 364.8~368.0 mm |
| C3 | 368.0~371.1 mm |
| C4 | 371.1~374.3 mm |
| C5 | 374.3~377.4 mm |
| C6 | 377.4~380.6 mm |
| C7 | 380.6~383.7 mm |
| C8 | 383.7~386.9 mm |
| C9 | 386.9~390.9 mm |
| D0 | 390.0~393.2 mm |
| D1 | 393.2~396.3 mm |
| D2 | 396.3~399.5 mm |
| D3 | 399.5~402.6 mm |
| D4 | 402.6~405.8 mm |
| D5 | 405.8~408.9 mm |
| D6 | 408.9~412.1 mm |
| D7 | 412.1~415.2 mm |
| D8 | 415.2~418.4 mm |
| D9 | 418.4~421.5 mm |
| E0 | 421.5~424.7 mm |
| E1 | 424.7~427.8 mm |
| E2 | 427.8~431.0 mm |
| E3 | 431.0~434.1 mm |
| E4 | 434.1~437.3 mm |
| E5 | 437.3~440.4 mm |
| E6 | 440.4~443.6 mm |
| E7 | 443.6~446.7 mm |
| E8 | 446.7~449.9 mm |
| E9 | 449.9~453.0 mm |
| F0 | 453.0~456.2 mm |

What is claimed is:

1. A multi-function test station for golf club shafts, comprising:
   a housing having a lower portion joined to an inclined wall joined to an upper portion;
   a rail extending along a length of the upper portion;
   four towers mounted on the rail to move along at least a portion of the length of the rail, each tower having a shaft positioning device oriented to center a longitudinal axis of the shaft in a common, substantially vertical plane, each shaft positioning device being vertically adjustable in position;

a force detecting device in each of two of the towers, the force detecting device detecting the force exerted on the shaft positioning device in the substantially vertical plane;

a display device in electronic communication with at least one of the force detecting devices to visually display indicia reflecting the force detected by the at least one force detecting device;

a fastening mechanism on each tower releasably fastening the tower to the rail;

an end stop mounted to the rail or the upper housing portion and extending across a portion of the substantially vertical plane;

a pair of laterally spaced apart jaws, each jaw having an upper and lower jaw, each jaw having notch aligned along a longitudinal axis and sized to clamp onto the shaft during use of the test station; and a mechanism actuating the jaws to open to receive a golf club shaft in the notches and to close on the golf club shaft to hold the shaft along the longitudinal axis during use.

2. The multi-function test station of claim 1, wherein two of the shaft positioning devices are configured to support a golf club shaft from below the shaft, and two of the shaft positioning devices are configured to engage the golf club shaft from at least the upper side of the shaft.

3. The multi-function test station of claim 1, wherein the shaft positioning device comprises a pair of rollers rotating on parallel but offset axes, with the rollers having cross sections that narrow to a reduced area at an outer periphery of the rollers, the rollers being spaced apart enough so they do not abut each other but close enough so the shaft cannot pass between them and rolls freely as the rollers rotate about their axes.

4. The multi-function test station of claim 2, wherein the shaft positioning device comprises a pair of rollers rotating on parallel but offset axes, with the rollers having cross sections that narrow to a reduced area at an outer periphery of the rollers, the rollers being spaced apart enough so they do not abut each other but close enough so the shaft cannot pass between them and rolls freely as the rollers rotate about their axes.

5. A multi-function test station for golf club shafts, comprising:

a housing having a lower portion joined to an inclined wall joined to an upper portion;

a rail extending along a length of the upper portion;

four towers mounted on the rail to move along at least a portion of the length of the rail, each tower having a shaft positioning device oriented to center a longitudinal axis of the shaft in a common, substantially vertical plane, each shaft positioning device being vertically adjustable in position;

a force detecting device in each of two of the towers, the force detecting device detecting the force exerted on the shaft positioning device in the substantially vertical plane;

a display device in electronic communication with at least one of the force detecting devices to visually display indicia reflecting the force detected by the at least one force detecting device;

a fastening mechanism on each tower releasably fastening the tower to the rail;

an end stop mounted to the rail or the upper housing portion and extending across a portion of the substantially vertical plane; and a pull-out drawer located below the lower portion of the housing and extendable away from the rail, the drawer containing a linear scale extending along a length of the drawer, the linear scale having a rotating stop at one end of the scale to align with an inclined portion of a club head mounted to the shaft, the linear scale having an alignment mechanism to align the shaft along the scale when the inclined portion of the club head is aligned with the rotating stop during use of the test station.

6. The multi-function test station of claim 1, further comprising a pair of posts on opposing sides of the longitudinal axis with a vibration sensor located on at least one of the posts to determine the vibration frequency of a shaft extending along the longitudinal axis during use of the test station; and a sensor track extending along a length of the lower portion below the longitudinal axis;

a support stand having a first end movably mounted to the track to move along that sensor track and having an opposing end to which is another shaft positioner.

7. The multi-function test station of claim 6, further comprising a weight configured to be releasably fastened to the end of a golf club shaft during use of the test station.

8. The multi-function test station of claim 6, further comprising a torsional frequency sensor on the housing or one of the towers and a torsional weight configured to be releasably fastened to the end of a golf club shaft during use of the test station, the torsional weight having a surface that interacts with the torsional frequency sensor to detect torsional frequency of a shaft to which the torsional weight is fastened during use of the test station.

9. The multi-function test station of claim 1, further comprising a pull-out drawer located below the lower portion of the housing and extendable away from the rail, the drawer containing a linear scale extending along a length of the drawer, the linear scale having a rotating stop at one end of the scale to align with an inclined portion of a club head mounted to the shaft, the linear scale having an alignment mechanism to align the shaft along the scale when the inclined portion of the club head is aligned with the rotating stop during use of the test station.

10. The multi-function test station of claim 9, wherein the rotating stop comprises two stops at 90° to each other rotating about a common pivot point at the end of the linear scale, and further comprising an angular scale centered on the pivot point with visible indicia reflecting the angle of each stop.

11. The multi-function test station of claim 6, further comprising a pull-out drawer located below the lower portion of the housing and extendable away from the rail, the drawer containing a linear scale extending along a length of the drawer, the linear scale having a rotating stop at one end of the scale to align with an inclined portion of a club head mounted to the shaft, the linear scale having an alignment mechanism to align the shaft along the scale when the inclined portion of the club head is aligned with the rotating stop during use of the test station.

12. A test station for testing golf clubs, comprising:

an elongated base having a first lower portion and a top portion vertically and horizontally offset from the first portion;

a clamp on the lower portion configured to releasably hold an end of a golf club shaft so the shaft extends along a first axis during use of the test station;

a vibration sensor located along the first axis to detect vibration of a shaft positioned along that first axis, the vibration sensor in communication with a display on the base to display vibration information during use;

a torsion sensor located on the base to detect torsion of a shaft positioned along that first axis, the torsion sensor in communication with a display on the base to display torsion information during use;

a first, second, third and fourth towers sequentially located on and movably connected to a rail extending along the top portion of the base, the first and third towers each having a first vertically adjustable shaft positioner and each also having a device to detect forces exerted on the first shaft positioner along a vertical axis, the second and fourth towers each having a second vertically adjustable shaft positioner, with the devices to detect forces each being in communication with a display to display the forces detected during use; and an elongated drawer in the base, below the lower section, the drawer having a linear scale extending along a length of the drawer with an angular measurement device at one end of the scale to measure the length of the club shaft and the lie angle of a golf club head on that shaft, respectively.

13. The test station of claim 12, wherein at least some of the shaft positioners comprise a pair of rollers on parallel axes spaced apart a distance sufficient to allow a shaft to rest on the rollers between the axes and freely rotate with the rollers.

14. The test station of claim 12, wherein the towers each have a quick release connection to releasably fasten the tower to the rail.

15. The multi-function test station of claim 5, wherein the rotating stop comprises two stops at 90° to each other rotating about a common pivot point at the end of the linear scale, and further comprising an angular scale centered on the pivot point with visible indicia reflecting the angle of each stop.

16. The test station of claim 12, wherein the angular measurement device comprises two stops 90° to each other and rotating about a pivot point at the end of the linear scale, with an angular scale centered on the pivot point and the angular scale having with visible indicia reflecting the angle of each stop.

17. The test station of claim 12, wherein the drawer further contains a pair of offset counterweights configured to attach to an end of a golf club shaft during use to impart torsional rotation to the shaft and a motion detector located on the test station to detect periodic passage of one of the counterweights.

18. The test station of claim 12, further comprising an end stop connected to the rail with a quick connect mechanism, the end stop located so the end of a golf club can abut the end stop when the club is in the generally horizontal position.

19. The test station of claim 18, wherein the stop has a releasable connection allowing the stop to rotate its position to avoid interference with a shaft extending along a length of the top during use of the test station.

20. The test station of claim 13, wherein, when the second and fourth towers are configured to support a golf club horizontally with a spacing of 14 inches between the supports on the second and fourth towers, the swing weight of the shaft is about 0.0897 times the force detected by the force detection device on the second tower which device is located adjacent a grip end of the club.

21. A test station for testing golf clubs, comprising:

an elongated base having a first lower portion and a top portion vertically and horizontally offset from the first portion;

a clamp on the lower portion configured to releasably hold an end of a golf club shaft so the shaft extends along a first axis during use of the test station;

a vibration sensor located along the first axis to detect vibration of a shaft positioned along that first axis, the vibration sensor in communication with a display on the base to display vibration information during use;

a torsion sensor located on the base to detect torsion of a shaft positioned along that first axis, the torsion sensor in communication with a display on the base to display torsion information during use;

a first, second, third and fourth towers sequentially located on and movably connected to a rail extending along the top portion of the base, the first and third towers each having a first vertically adjustable shaft positioner and each also having a device to detect forces exerted on the first shaft positioner along a vertical axis, the second and fourth towers each having a second vertically adjustable shaft positioner, with the devices to detect forces each being in communication with a display to display the forces detected during use; and wherein the stop has a releasable connection allowing the stop to rotate its position to avoid interference with a shaft extending along a length of the top during use of the test station.

22. A multi-function test station for golf club shafts, comprising:

a housing having a lower portion joined to an inclined wall joined to an upper portion;

a rail extending along a length of the upper portion;

four towers mounted on the rail to move along at least a portion of the length of the rail, each tower having a shaft positioning device oriented to center a longitudinal axis of the shaft in a common, substantially vertical plane, each shaft positioning device being vertically adjustable in position;

a force detecting device in each of two of the towers, the force detecting device detecting the force exerted on the shaft positioning device in the substantially vertical plane;

a display device in electronic communication with at least one of the force detecting devices to visually display indicia reflecting the force detected by the at least one force detecting device;

a fastening mechanism on each tower releasably fastening the tower to the rail;

an end stop mounted to the rail or the upper housing portion and extending across a portion of the substantially vertical plane; and wherein at least some of the shaft positioners comprise a pair of rollers on parallel axes spaced apart a distance sufficient to allow a shaft to rest on the rollers between the axes and freely rotate with the rollers and wherein, when the second and fourth towers are configured to support a golf club horizontally with a spacing of 14 inches between the supports on the second and fourth towers, the swing weight of the shaft is about 0.09 times the force detected by the force detection device on the second tower which device is located adjacent a grip end of the club.

* * * * *